United States Patent [19]

Sauk et al.

[11] Patent Number: 4,698,326

[45] Date of Patent: Oct. 6, 1987

[54] COMPOSITION AND METHOD FOR OSSEOUS REPAIR

[75] Inventors: John J. Sauk, Ellicott, Md.; Craig L. Van Kampen, Oakdale, Minn.

[73] Assignees: Regents of the University of Minnesota, Minneapolis; Minnesota Mining and Manufacturing Company, St. Paul, both of Minn.

[21] Appl. No.: 811,677

[22] Filed: Dec. 20, 1985

[51] Int. Cl.$^4$ ............................................. A61K 37/16
[52] U.S. Cl. ............................................. 514/7; 514/2
[58] Field of Search ........................................ 514/2, 7

[56] References Cited

U.S. PATENT DOCUMENTS

| 2,968,593 | 1/1961 | Rapkin | 167/74 |
| 4,172,128 | 10/1979 | Thiele et al. | 424/95 |
| 4,294,753 | 8/1980 | Urist | 260/112 |
| 4,485,097 | 11/1984 | Bell | 424/95 |

FOREIGN PATENT DOCUMENTS 0082621  6/1983  European Pat. Off. .

OTHER PUBLICATIONS

Fujisawa et al—Chem. Abst. vol. 97 (1982) p. 68098w.
Cocking—Johnson et al—Chem. Abst. vol. 98 (1983) p. 48844D.
M. R. Urist et al., *Proc. Natl Acad. Sci. USA*, 76, 1828 (1979).
Debra Cocking-Johnson et al., *Collagen Rel. Res.*, 3, 505 (1983).
W. T. Butler et al., *Coll. Res.*, 1, 187 (1981).
M. R. Urist, *Science*, 150, 893 (1965).
Y. Kuboki et al., *J. Dent. Res.*, 58, 1926 (1979).

*Primary Examiner*—Sam Rosen
*Attorney, Agent, or Firm*—Merchant, Gould, Smith, Edell, Welter & Schmidt

[57] ABSTRACT

A composition and method for the repair of an osseous defect comprising introducing into said defect a phosphophoryn calcium salt, preferably in combination with a matrix material such as type I collagen.

13 Claims, No Drawings

COMPOSITION AND METHOD FOR OSSEOUS REPAIR

BACKGROUND OF THE INVENTION

Currently, the most effective method for treatment of severe or nonhealing osseous defects is autogenic bone grafting, which involves the transplantation of bone from another part of a patient's body into the defect. Significant disadvantages are associated with autogenic bone grafting, including donor site morbidity and limited tissue availability. Bone banks have been established to provide an alternative source of bone grafting material, consisting of allogenic freeze-dried bone. Allogenic bone grafts, however, are very expensive and do not heal as well as do fresh autogenic bone grafts.

Attempts to overcome these problems have involved the use of calcium phosphates and apatites, as well as derivatives of natural bone to initiate new bone formation. Tricalcium phosphate and apatites have generally been employed to physically support the newly formed bone. Although such materials have been disclosed to be useful for dimensional augmentation after subperiosteal implantations, it is believed that they tend to exhibit slow or incomplete healing.

Demineralized, lyophilized bone has also been used as a component of osteoinductive agents. See, M. R. Urist, Science, 150, 893 (1965). Recently, M. R. Urist et al., in U.S. Pat. No. 4,294,753 and in Proc. Natl. Acad. Sci. USA, 76, 1828 (1979) have disclosed the use of proteins derived from such bone matrices with various carriers to induce new bone formation. However, it can be difficult to reproducibly prepare these materials, which must be characterized by various bioassay systems.

Therefore, a need exists for compositions which are useful to repair osseous defects by promoting the formation of new bone therein. A further need exists for compositions useful for osseous repair which can be prepared reproducibly, e.g., which incorporate well characterized components.

SUMMARY OF THE INVENTION

The present invention is directed to compositions comprising the calcium salts of the mineral nucleating proteins known as phosphophoryns. Preferably these compositions will also include a physiologically-acceptable compound capable of providing a matrix for said salt. A preferred embodiment of this invention is a composition comprising a calcium salt of dentinal phosphophoryn and a suitable collagen. The present invention is also directed to the use of these compositions to promote bone formation upon their introduction into osseous defects.

Therefore, the compositions of the present invention are useful as bone graft substitutes in the repair of osseous defects and to promote osseous formation. For example, they are useful to fill defects created during the treatment of osteosarcomas or bone cysts, to promote the repair of nonunions and to repair alveolar clefts. The present compositions are readily reabsorbed in a short period after initiating a cascade of events which leads to their complete replacement by new bone. Furthermore, the present compositions are well-characterized and can be obtained reproducibly.

The compositions of the present invention are particularly useful for the treatment of large osseous defects, where there is a requirement for a rapid diminishment of an osseous void in order to re-establish the cortical plate and reduce the possibility of fracture.

DETAILED DESCRIPTION OF THE INVENTION

According to the present invention, new bone formation can be promoted in vivo in osseous defects by introduction thereinto of a composition comprising phosphophoryn calcium. To facilitate manipulation by the physician and to provide a structure to direct the deposition of new bone, these compositions preferably comprise a mixture of phosphophoryn calcium and a matrix material such as type I collagen. These compositions are intended to facilitate matrix-mediated mineralization, whereby the collagen defines a structural matrix and the phosphophoryn salt regulates and directs mineral deposition in terms of its location and crystallinity.

Thus, the present compositions do not simply provide a static physical "scaffold" for bone ingrowth, but are believed to create a dynamic ionic front that accelerates new bone formation by mimicking the mineralization front created by dentin in vivo. Another advantage of the invention is that the compositions are able to be absorbed after initiating a cascade of events that leads to a more rapid and complete replacement of osseous voids than can be accounted for by normal wound healing processes.

Phosphophoryn Salt

Phosphophoryns are acidic, phosphorous-containing proteins which can be isolated from the noncollagenous proteins which are constituents of the organic extracellular matrix of certain mineralized tissues. In vivo, these proteins may act to initiate the calcification of dentin by chelating calcium ions. Purified dentinal phosphophoryn has a high affinity for calcium ion. Its binding sites exhibit dissociation constants (Kd) of $1.3 \times 10^{-7}$M and $0.85 \times 10^{-5}$M. However, sodium, potassium and magnesium ions can effectively compete with $Ca^{+2}$ for these binding sites. The calcium salts of phosphophoryn employed in the present invention may reduce this deleterious competitive binding.

Conventional methods for the purification of the preferred dentinal phosphophoryn employ precipitation of decalcified dentin with calcium salts. Following purification, these salts can be employed as the dentinal phosphophoryn calcium component in the present compositions. The purification of dentinal phosphophoryn has been described by W. T. Butler et al., Collagen Rel. Res., 1, 187 (1981) and by D. Cocking-Johnson et al. in Collagen Rel. Res., 3, 505 (1983), the disclosures of which are incorporated by reference herein.

Synthetic phosphophoryns may be produced in the laboratory by recombinant DNA techniques. Alternatively, phosphophoryn analogs useful in the present invention may be chemically synthesized by conventional reactions employed in polypeptide synthesis.

Collagen

Collagen is the general designation for a group of at least four connective tissue proteins, which are designated as types I-IV. Type I collagen accounts for a large part of the organic mass of bone, and has also been isolated from intervertebral disc, liver, tendon and kidney tissue, and in combination with type III collagen from skin, sclera and spleen. The precipitational behavior of native pepsin-resistant collagen molecules at relatively low ionic strength has been used extensively for their purification from other proteins. In addition, differential solubilities have been observed for types I, II and III collagens which can be fractionated from one another by precipitation at different salt concentrations at neutral pH. For example, at acidic pH's, both type I collagen and type III collagen derived from skin precipitate at 0.7–0.9M NaCl concentration, while at neutral pH, type I precipitates in 2.6M NaCl while type III precipitates in 1.5–1.7M NaCl. See E. H. Epstein, Jr., J. Biol. Chem., 249, 3225 (1974).

Due to the difficulties encountered in preparing pure collagen of a given type, the term "type I collagen" as used herein is intended to refer to pure type I collagen and any collagen preparation which comprises a substantial proportion of type I collagen, preferably at least a major proportion of type I collagen.

The preferred compositions are prepared by mixing dentinal phosphophoryn calcium with type I collagen in weight ratios of the calcium salt to the collagen of about 3.0–0.1:1, preferably about 2.5–0.5:1, most preferably about 1:1. The mixtures can be prepared by adding the desired amount of the phosphophoryn calcium salt as a powder to an aqueous solution containing the desired amount of collagen and removing the water in vacuo. The resultant material is a brown, hardened sponge which can be directly implanted into osseous defects without further purification.

To evaluate the ability of the present compositions to repair osseous defects, phosphophoryn calcium and a composition comprising a 1:1 mixture of bovine skin collagen and phosphophoryn calcium were implanted within 6.0 mm² parietal defects in guinea pig skulls, as described in Example I, hereinbelow. The results from a study in which 6 mm² defects were treated indicates that complete closure of the wound site by osteoid of a thickness greater than one half the thickness of the original bone occurred within two weeks. This degree of healing was significantly greater than that observed in control animals which were permitted to heal normally. The study clearly indicated that both phosphophoryn calcium and the calcium phosphophoryn-collagen mixture had a direct effect on promoting osteoid replacement within these flat bones.

In a second study, the guinea pig parietal bone defects were extended to at least 1.5 cm², as described in Example II, hereinbelow. In this study, 12 control and 48 treated animals were evaluated in a one month study. Closures of the wounds among the controls occurred throughout approximately 7% of the area of the defects. The group treated with a 1:1 mixture of type I collagen and phosphophoryn calcium exhibited a 30% area closure by new bone formation.

The invention will be further described by reference to the following detailed examples.

EXAMPLE I

Repair of 6 mm² Parietal Bone Defects

1. Materials

A. Lyophilized, Demineralized Bone

Fresh bovine cortical bone was obtained and frozen at −70° C. The bone was cryoground and mesh-sized. The resultant fragments were then extracted with chloroform/ methanol 1:1, and decalcified in EDTA and guanidine hydrochloride at 4° C. Following demineralization the fragments were washed extensively and lyophilized.

B. Dentinal Phosphophoryn Calcium Salts

Small pieces of cleaned bovine dentin were stirred for 18 hr at 4° C. in 4M guanidine-HCL containing four protease inhibitors [1 mM iodoacetate, 1 mM phenylmethylsulfonyl fluoride (PMSF), 1 mg/ml soybean trypsin inhibitor and 5 mM n-ethylmaleimide ]. The dentin was rinsed thoroughly with water, placed in dialysis bags and decalcified by dialysis against 0.25M EDTA containing the protease inhibitors at 4° C. Decalcification required a minimum of 3 changes of EDTA, each exposure lasting at least 72 hours. The supernatant inside the dialysis bags was isolated and dialyzed against distilled water for at least 4 days. The phosphophoryns were then precipitated with calcium chloride as described by Y. Kuboki et al., J. Dent. Res., 58, 1926 (1979) and the mixture was stirred for 18 hr at 25° C. The dentinal phosphophoryn calcium salts were isolated by centrifugation, washed with 1.0M aqueous $CaCl_2$ and dried by lyophilization.

C. Unenriched Bovine Skin Collagen

Bovine skin was digested with 1 mg/ml pepsin and the crude product precipitated with NaCl (0.7 M). The collagen was then dialyzed extensively against 0.5 M acetic acid and lyophilized. The supernatant was treated with NaCl (1.5M) to yield a precipitate which was dialyzed extensively against 0.5M acetic acid and lyophilized to yield the product.

D. Type I- and Type III- Collagen

Collagen was prepared from bovine skin by the procedure of Uitto as described in *Arch. Biochem. & Biophys.*, 371–379 (1979). Accordingly, samples of calf skin were dissected and the subcutaneous tissues removed. The specimens were then rinsed with cold (+4° C.) 0.15 M NaCl–0.05 M Tris-HCl, pH 7.5. The skin was then minced extensively with scissors in 0.5 M acetic acid. Pepsin (Worthington Diagnostics, Freehold, NJ, 2× crystallized) was added to a final concentration of 0.1 mg/ml, and the samples were incubated at 4° C. for 16 hr. At the end of the incubation period, the homogenate was centrifuged at 30,000 g for 60 min at 4° C. The pellet was then dissolved and adjusted to pH 8.5 with cold 1.0 M NaOH, and extensively dialyzed against 0.4 M NaCl–0.1 M Tris-HCl, pH 7.5.

In order to separate type I collagen, the solubilized material was fractionated by the sequential precipitations with 1.5 and 2.5 M NaCl. After the slow addition of solid NaCl to any given concentration, the samples were stirred for 24 hr at 4° C. and then centrifuged at 30,000 g for 60 minutes.

The pellet resulting from precipitation at 2.5 M NaCl was dissolved in and dialyzed against 0.5 M acetic acid and then lyophilized. The type I-enriched collagen appears as a soft white spongy substance.

The pellet resulting from the precipitation with 1.5 M NaCl at neutral pH consists of a 1:1 distribution of type I and type III collagen. See J. Uttio, Arch. Biochem. Biophys., 192, 371 (1979).

E. Osseous Repair Compositions

Unenriched bovine skin collagen, bovine type I collagen or a 1:1 mixture of type I and type III collagen were dissolved in 0.5M acetic acid at 4° C. for 24hr with constant mixing. The resulting solutions were then centrifuged at 30,000 g for 30 minutes and the supernatant collected. The concentration of the collagen was adjusted to 1 mg/ml by measuring the absorption at 247 nm for which a standard curve has been created based on absorption and hydroxyproline ratios. To these latter collagen solutions 1 mg/ml of phosphophoryn calcium was added. The resulting mixtures were then stirred vigorously, since the phosphophoryn calcium is insoluble, and shell frozen at −20° C. using acetone and dry ice. The resulting osseous repair mixtures were lyophilized and stored in a sealed container at −70° C. The materials appear as light brown, hardened sponges.

2. Surgical Procedures

Guinea pigs, 200 grams in weight, were quarantined for at least 3 days prior to surgery. After administration of general anesthesia, an incision was made between the ears extending toward the nose to expose both parietal bones. Using a dental handpiece and surgical bone bur, 6 mm$^2$ circular defects were made extending to the meninges. At least 2 to 4 defects were placed in each animal. The defects in five groups of guinea pigs were then filled with (a) decalcified bone (25 defects), (b) unenriched collagen (7 defects), (c) phosphophoryn calcium (23 defects) or (d) the phosphophoryn calcium-unenriched collagen composition (13 defects). Thirty guinea pigs were left untreated for use as controls. The incisions were then sutured and the animals housed as before. One or two weeks after surgery, the animals were sacrificed by cardiac puncture after being administrated a lethal dose of sodium barbitol. The parietal bones were removed, decalcified, and paraffin-embedded. Sections of each defect were prepared and stained with hematoxylin and eosin.

3. Scoring of the Defects

The extent of healing of a given parietal defect was assigned a score of 0–6 on the bases summarized on Table I.

TABLE I

| Score | Extent of Wound Closure |
|---|---|
| 0: | No new bone formation or repair present. |
| 1: | Less than one third of the defect was replaced by new bone or osteoid. |
| 2: | Less than two thirds of the bony defect was replaced by new bone or osteoid. |
| 3: | More than two thirds, but less than complete closure of the wound site by new bone or osteoid. |
| 4: | Complete closure of the wound site by new bone or osteoid, less than one half of the normal thickness. |
| 5: | Complete closure of the wound site by new bone or osteoid of a thickness greater than one half of normal. |
| 6: | Complete closure of wound site by new bone or osteoid to a normal or greater than normal thickness of cortical bone. |

In each instance, data were collected from at least 2 sections. All of the slides were coded, read, and scored randomly. The resulting data were then tabulated and comparisons between the groups were judged by Student t-tests.

4 Results

A. Control vs. Decalcified Bone

The extent of the repair of the control bony defects scored 1.84 with a standard deviation (SD) of 1.1 and a standard error of mean (SEM) of 0.22. This compared to a mean closure score of 2.53 for decalcified bone (SD=1.52, SEM=0.27). The comparative healing observed for these two groups was judged to be not significant.

B. Control vs. Collagen

Compared to control, the collagen filled defects scored a repair mean of 3.57 (SD=1.40, SEM=0.53). These data indicated that collagen had a significant positive effect on bone healing.

C. Control vs. Phosphophoryn Calcium

Compared to control the phosphophoryn calcium salts scored 3.57 (SD=1.47, SEM=0.31). Thus, the phosphophoryn calcium also exhibited a statistically significant positive effect upon bone healing.

D. Phosphophoryn Calcium-Unenriched Collagen Mixture

The mean healing score for this group was 4.15 (SD=1.72, SEM=0.48). This was the most highly significant and positive healing observed of all the groups tested.

EXAMPLE II. Repair of 1.5 cm$^2$ Parietal Defects

The parietal bones of guinea pigs were exposed as described in Example I. Using a dental handpiece and a surgical bone bur, four bur holes were connected to provide a defect of approximately 1.5 cm$^2$. The defects in two groups of 16 animals were then filled with (a) a 1:1 mixture of phosphophoryn calcium and type-I collagen or (b) a 1:1 mixture of phosphophoryn calcium and a mixture (1:1) of type I and type III collagen. Twelve animals were employed as untreated controls. The animals were then sacrificed at one month.

The extent of osseous repair among the controls occurred through 6.7% of the area of the defects (SD=7.4, SEM=2.1). The group treated with a mixture of type I and type III collagen and phosphophoryn calcium had only 2.5% of the defect replaced by osteoid after one month (SD=2.7, SEM=1.12). In contrast, the group treated with type I collagen and phosphophoryn calcium achieved approximately 30% of new bone matrix within the surgical defects during the identical period (SD=5.8, SEM=2.39).

SUMMARY

Examples I and II clearly demonstrate that the calcium salt of phosphophoryn has a positive effect on bone formation. In particular, the type I collagen-phosphophoryn calcium mixtures of Example II have a positive effect on the healing of parietal bony defects. In the large defects of Example II, the healing process was 30% complete at one month, far exceeding the 7% healing observed in the controls.

The invention has been described with reference to various specific and preferred embodiments and techniques. However, it should be understood that many variations and modifications may be made while remaining within the spirit and scope of the invention.

What is claimed is:

1. A composition for osseous repair which is prepared by a process comprising mixing a phosphophoryn calcium salt and type I collagen in a ratio of the phosphophoryn calcium salt to the type I collagen of about 3.0–0.1:1 to yield a solid composition which is effective to promote new bone formation upon introduction of the composition into osseous defects.

2. The composition of claim 1 wherein the mixture contains a dentinal phosphophoryn calcium salt.

3. The composition of claim 1 wherein the weight ratio of the dentinal phosphophoryn calcium salt to the type I collagen is about 1:1.

4. The composition of claim 1 wherein a mixture of the phosphophoryn calcium salt and the type I collagen in water is prepared and the water is removed in vacuo.

5. The composition of claim 2 wherein the water is removed by lyophilization.

6. A method for the repair of an osseous defect comprising introducing into said defect a composition comprising an amount of a phosphophoryn calcium salt effective to promote new bone formation.

7. A method for the repair of an osseous defect comprising introducing into said defect a composition comprising a mixture of a phosphophoryn calcium salt and type I collagen effective to promote new bone formation.

8. An osseous repair implant which is prepared by a process comprising introducing an amount of a solid composition containing an amount of a phosphophoryn calcium salt effective to promote new bone formation in an osseous defect having an exposed surface so that said composition presents a surface opposing and conformed to the exposed surface of said defect.

9. The composition of claim 8 wherein said composition fills said defect.

10. The composition of claim 8 wherein the composition contains a dentinal phosphophoryn calcium salt.

11. The composition of claim 10 wherein the composition contains type I collagen.

12. The composition of claim 11 wherein the weight ratio of the phosphophoryn calcium salt to the type I collagen is about 3.0–0.1:1.

13. The composition of claim 12 wherein the weight ratio of the phosphophoryn calcium salt to the type I collagen is about 1:1.

* * * * *